(12) United States Patent
Bondurant et al.

(10) Patent No.: US 10,408,796 B2
(45) Date of Patent: Sep. 10, 2019

(54) COMBINED ELECTROMAGNETIC ACOUSTIC TRANSDUCER (EMAT) AND ELECTRO PERMANENT MAGNETS (EPMS) FOR BIAS FIELD CONTROL

(71) Applicant: Quest Integrated, LLC, Kent, WA (US)

(72) Inventors: Phillip Dewayne Bondurant, Covington, WA (US); Anthony Mactutis, Auburn, WA (US); Giovanni Nino, Issaquah, WA (US)

(73) Assignee: Quest Integrated, LLC, Kent, WA (US)

( * ) Notice: Subject to any disclaimer, the term of this patent is extended or adjusted under 35 U.S.C. 154(b) by 125 days.

(21) Appl. No.: 15/488,285

(22) Filed: Apr. 14, 2017

(65) Prior Publication Data

US 2017/0299554 A1 Oct. 19, 2017

Related U.S. Application Data

(60) Provisional application No. 62/322,543, filed on Apr. 14, 2016.

(51) Int. Cl.
*G01N 29/04* (2006.01)
*G01N 29/24* (2006.01)

(52) U.S. Cl.
CPC ......... *G01N 29/2412* (2013.01); *G01N 29/04* (2013.01); *G01N 2291/101* (2013.01)

(58) Field of Classification Search
CPC ............... G01N 29/2412; G01N 29/04; G01N 2291/101

USPC .......................................................... 73/643
See application file for complete search history.

(56) References Cited

U.S. PATENT DOCUMENTS

| | | | | |
|---|---|---|---|---|
| 5,087,844 | A * | 2/1992 | Takedomi | H02K 41/031 310/12.01 |
| 7,697,375 | B2 * | 4/2010 | Reiderman | B06B 1/04 367/168 |
| 7,726,193 | B2 | 6/2010 | Reiderman et al. | |
| 2007/0151344 | A1 * | 7/2007 | Meethal | G01N 29/2412 73/649 |
| 2010/0199767 | A1 * | 8/2010 | Ganin | G01N 29/225 73/623 |
| 2011/0259108 | A1 * | 10/2011 | Ege | B06B 1/04 73/643 |
| 2012/0049848 | A1 * | 3/2012 | Rapoport | G01R 33/3802 324/318 |
| 2012/0240681 | A1 * | 9/2012 | Lopez Jauregui | G01N 29/043 73/643 |

\* cited by examiner

*Primary Examiner* — Jacques M Saint Surin
(74) *Attorney, Agent, or Firm* — Christensen O'Connor Johnson Kindness PLLC (57) ABSTRACT

Systems and methods for non-destructive testing of specimens are disclosed herein. In one embodiment, an electromagnetic acoustic transducer (EMAT) includes an electro-permanent magnet (EPM) configured to controllably apply a biasing magnetic flux to a target location. The EPM includes a hard magnet, and a soft magnet at least partially enclosing the hard magnet. The EPM also includes a magnetizing coil having a plurality of turns at least partially encircling the soft magnet. The magnetizing coil is configured to controllably magnetically bias the soft magnet when a current is applied to the magnetizing coil.

24 Claims, 12 Drawing Sheets

COMBINED ELECTROMAGNETIC ACOUSTIC TRANSDUCER (EMAT) AND ELECTRO PERMANENT MAGNETS (EPMS) FOR BIAS FIELD CONTROL

CROSS-REFERENCE TO RELATED APPLICATION

This application claims the benefit of Provisional Application No. 62/322,543, filed Apr. 14, 2016, which is incorporated herein by reference.

BACKGROUND

Electromagnetic Acoustic Transducers (EMATs) are commonly used for non-destructive testing of metal structures. The EMATs can measure wall or plate thickness, and can detect cracks or other non-uniformities within the specimen. Material flaws can be caused by fatigue, corrosion, erosion, pitting, or wear. Flaws can also result from a fault in the manufacturing process. An advantage of using EMAT compared to conventional ultrasonic transducers (UT) is that the ultrasonic energy is transferred directly into the material of the specimen. Furthermore, while conventional UT requires a coupling gel or liquid to transfer the energy from the transducer to the object to be inspected, the EMAT based technologies do not require the coupling gel or liquid.

Figure 1:
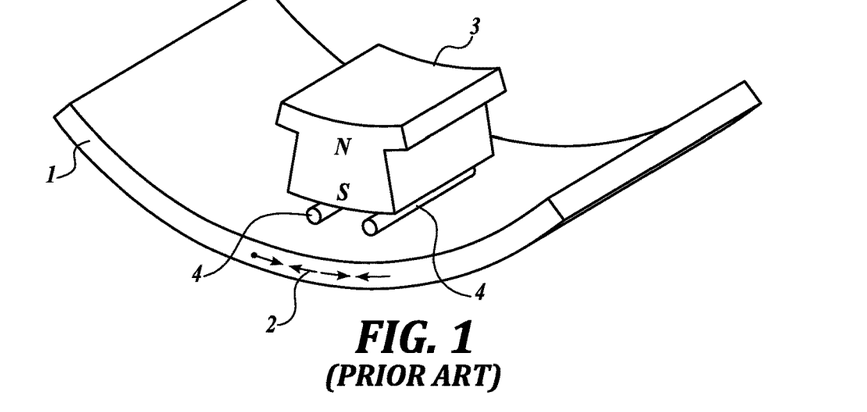
FIG. 1 is a schematic view of prior art EMAT transducer.

FIG. 1 shows a conventional EMAT transducer. A magnet 3, which can be a permanent magnet or an electromagnet, generates a biasing magnetic field over a sensor coil 4 that carries an alternating electrical current. The sensor coil 4 is placed near the object 1 to be inspected (also referred to as a specimen or a pipe). Interaction between the biasing magnetic field and the electrical current in the sensor coil 4 ultimately produces a radiating acoustic field 2 within the object to be inspected. By the principle of reciprocity, the reflected acoustic field in the object 1 can interact with a biasing magnetic field to produce a magnetic field that can now induce another current in the sensor coil 4. This combined transmit and receive capability of the sensor coil 4 provides a method of acoustically detecting and measuring flaws in the object to be inspected.

EMAT transducers commonly use strong permanent magnets (e.g., the magnet 3) to produce the required biasing magnetic field. In some situations, the electromagnets replace the permanent (also referred to as "hard") magnets. However the electromagnets require magnetizing coils with a large number of turns and need to maintain high currents for the duration of measurement. Because the magnetizing coil is an inductor, it also takes a certain amount of time for the current to reach the necessary levels for the magnetization. Additionally, the high electrical current generates heat that is difficult to dissipate. Therefore, the electromagnets typically need some form of cooling or are only usable for low duty-cycle applications where the ratio of the on-time to the off-time is small. Even if the duty cycle is low, heat dissipation can still be a problem if a single on-time event lasts long time. For wall thickness measurements, the on-time for single measurements might be on the order of 50 µs, however for a long range guided wave application, the sensor may need to be active for 10's milliseconds. In addition, to minimize resistance losses over long distances, wiring needs to have large diameter and thick electrical insulation, resulting in bulky cables that are difficult to handle. As a result, the use of hard magnets is preferred for most applications.

Conventional EMATs that use hard magnets also have some drawbacks. For example, EMAT based tools need to be shipped around the world in a timely fashion. However, transportation of the magnetic material by aircraft is regulated because the magnetic materials are considered hazardous. For example, according to the Federal Aviation Administration (FAA) regulations, the shipper of the magnetized materials must ensure that the package generates a magnetic field strength of less than 0.00525 gauss when measured at 15 feet from any surface of the package. For the packages having magnetic field less than 0.00525 gauss when measured at 15 feet, but greater than 0.002 gauss when measured 7 feet from the package, the package must be labeled "magnetic." As a comparison, the Earth's magnet field strength is approximately 0.5 Gauss. Therefore, in many cases the shipping box must be shielded, or the strength of the magnetic field must be reduced by putting magnetic shorting bars or "keepers" between the poles of the magnet. This is expensive, and results in a heavier shipment and a more time-consuming process for the operator or the shipper.

Furthermore, when the EMAT equipment is transported either by hand or machine to the object to be inspected, care must be taken to assure that ferromagnetic materials near the equipment are kept at a safe distance. Additionally, if the EMAT transducer is handheld or integrated into a portable tool that is attached to a ferromagnetic plate or inserted into a ferromagnetic pipe, the tool is difficult to handle due to the attraction between the strong magnet(s) integrated into the tool and the plate/pipe. Strong magnetic force may create safety issues as well, especially if fingers or other body parts get trapped between the magnets or between the magnets and ferromagnetic objects.

During the transport or use of the EMAT tools, the magnetic fields attract ferromagnetic debris that needs to be removed periodically to maintain proper operation of the tool. This cleaning is a time-consuming process, and may be difficult to perform. In addition, the overall tool design may need special provisions for the cleaning, for example by assuring that there are no slots or empty space where ferromagnetic debris accumulates.

Figure 2A:
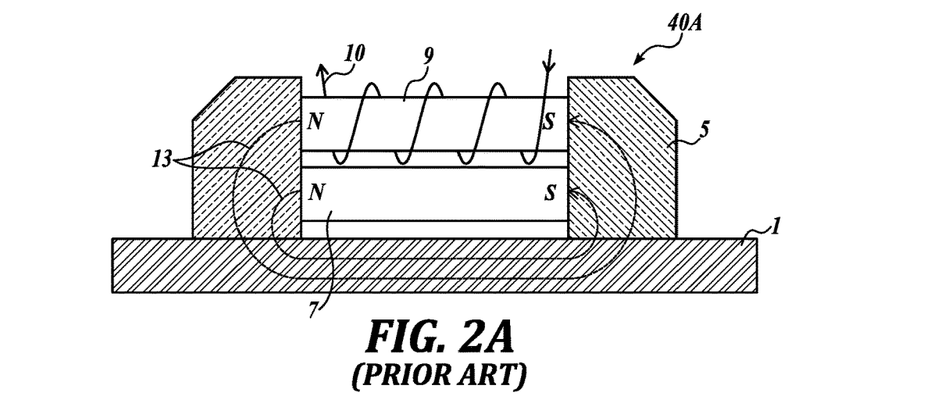
FIGS. 2A and 2B are schematic views of prior art electro-permanent magnet (EPM) in operational and transportation configurations, respectively.

FIG. 2A is schematic view of a prior art electro-permanent magnet (EPM) 40A in the operational configuration. EPMs are known alternatives to electromagnets and hard magnets. The transducer 40A includes a hard magnet 7 and an electromagnet 9 that can be polarized using a magnetizing coil 10. FIG. 2A illustrates the electromagnet 9 that is polarized to have N-S orientation that corresponds to that of the hard magnet 7. As a result, a magnetic flux 13 is strengthened. Yoke 5 conducts the magnetic flux 13 into the test specimen 1.

Figure 2B:
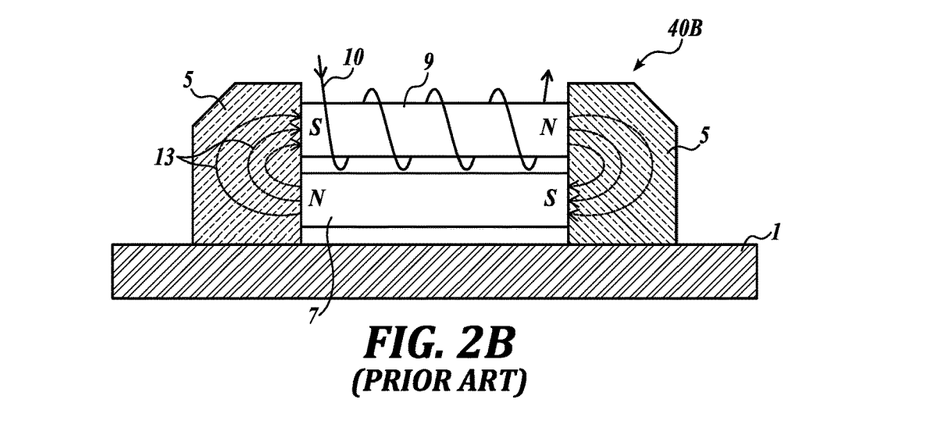

FIG. 2B is schematic view of a prior art electro-permanent magnet (EPM) 40B in the transportation configuration. The polarity of the electromagnet 9 is now inverted to be opposite to that of the hard magnet 7, i.e., the electromagnet 9 is switchable. As a result, the magnetic flux 13 travels from one magnet to another through the yoke 5 because this is a path of the least resistance for the magnetic flux. Since the magnetic flux 13 is generally constrained within the yoke 5, the leakage of the magnetic flux 13 outside of the EPM is minimized, and the electro-permanent magnet (EPM) 40B is suitable for transportation.

However, the electro-permanent magnet (EPM) 40A/40B is relatively bulky, resulting in increased cost/difficulty of transportation. Accordingly, there remains a need for compact EMAT tools that can produce strong magnetic field when the EMAT operates, while reducing or eliminating the leakage of the magnetic field when the EMAT is not in operation.

SUMMARY

The foregoing aspects and many of the attendant advantages of this invention will become more readily appreciated as the same become better understood by reference to the following and detailed description, when taken in conjunction with the accompanying drawings.

In some embodiments, an electromagnetic acoustic transducer (EMAT) includes: an electro permanent magnet (EPM) configured to controllably apply a biasing magnetic flux to a target location. The EPM includes a hard magnet, a soft magnet at least partially enclosing the hard magnet, and a magnetizing coil having a plurality of turns at least partially encircling the soft magnet. The magnetizing coil can be configured to controllably magnetically bias the soft magnet when a current is applied to the magnetizing coil. The EPM can include a sensor coil configured to provide an alternating magnetic field to the target location. The EMAT can be configured to controllably coordinate the EPM and the sensor coil to perform non-destructive testing of the target location.

In one aspect, the hard magnet, the soft magnet, and the magnetizing coil are coaxially aligned perpendicular to the target location.

In one aspect, the hard magnet, the soft magnet, and the magnetizing coil are coaxially aligned parallel to the target location.

In another aspect, the EMAT includes a yoke for providing magnetic communication between a first end and a second end of the EPM.

In one embodiment, a method of operating an EMAT includes: passing a first pulse of electrical current through a magnetizing coil adjacent to a soft magnet of an electro-permanent magnet (EPM); in response to passing the first pulse of electrical current, polarizing the soft magnet to a first polarization, where the soft magnet at least partially encloses a hard magnet of the EPM, and where the hard magnet is in the first polarization; and passing a second pulse of electrical current through the magnetizing coil adjacent to the soft magnet. The method further includes, in response to passing the second pulse of electrical current, polarizing the soft magnet to a second polarization, where the second polarization is opposite from the first polarization.

In one aspect, a magnetic flux is directed to a sensor coil of the EMAT.

In another aspect, acoustic waves are generated to perform a non-destructive testing of a specimen at a target location.

In another aspect, a flaw can be detected in the specimen based on reflected acoustic waves.

In one aspect, passing the first pulse of electrical current is done in preparation for the non-destructive testing of the specimen.

In another aspect, passing the second pulse of electrical current is done in preparation for repositioning or shipping of the EMAT.

DESCRIPTION OF THE DRAWINGS

The foregoing aspects and many of the attendant advantages of this invention will become more readily appreciated as the same become better understood by reference to the following and detailed description, when taken in conjunction with the accompanying drawings, wherein.

DETAILED DESCRIPTION

The inventive technology relates to an EMAT (electromagnetic acoustic transducer) sensor that is compact and can achieve a relatively high magnetic flux density. The inventive technology can be used in, for example, gas pipelines or empty pipes that lack a liquid couplant required for traditional pipe inspection systems.

In some embodiments, the inventive EMAT includes a concentric arrangement of a permanent magnet (also referred to as a hard magnet) and a soft magnet (e.g., a ferromagnetic core that can be magnetized with a pulse of electrical current). Before operation, the soft magnet may be polarized to have the same polarity as the hard magnet. Since the magnets are arranged concentrically (i.e., coaxially), a relatively high value of combined magnetic flux density is achievable. In some embodiments, after the initial polarization of the soft magnet, no additional electrical current needs to flow through the magnetizing coil, therefore minimizing heating of the EMAT. After the measurements, the polarity of the soft magnet can be reversed to be opposite from the polarity of the hard magnet. Since the hard magnet and the soft magnet can be relatively close to each other, the magnetic flux flows through the yoke from one magnet to another, thus minimizing leakage of the magnetic field to the environment. Therefore, in at least some embodiments, the leakage of the magnetic flux outside of the EMAT is minimized, which simplifies repositioning of the EMAT inside the pipe and transportation of the EMAT.

In some embodiments, due to the switchability of the EMAT, less ferromagnetic debris will accumulate, because in the "transportation" configuration no significant magnetic flux will leak outside of the EMAT. In some embodiments, the locations of the hard/soft magnet are interchangeable with relatively small design modifications while retaining relatively high levels of magnetic flux. Generally, the coaxial arrangement of the magnets causes relatively high strength of the magnetic flux at the sensor coil. Also, the coaxial arrangement of the magnets results in a lighter weight of the EMAT. In some embodiments, the hard magnet can be the inner magnet, surrounded by the soft magnet with the magnetizing coil wrapped around both magnets. Other arrangements are also possible, for example, the soft magnet being in the center, surrounded by the peripherally disposed hard magnet.

Figure 3A:
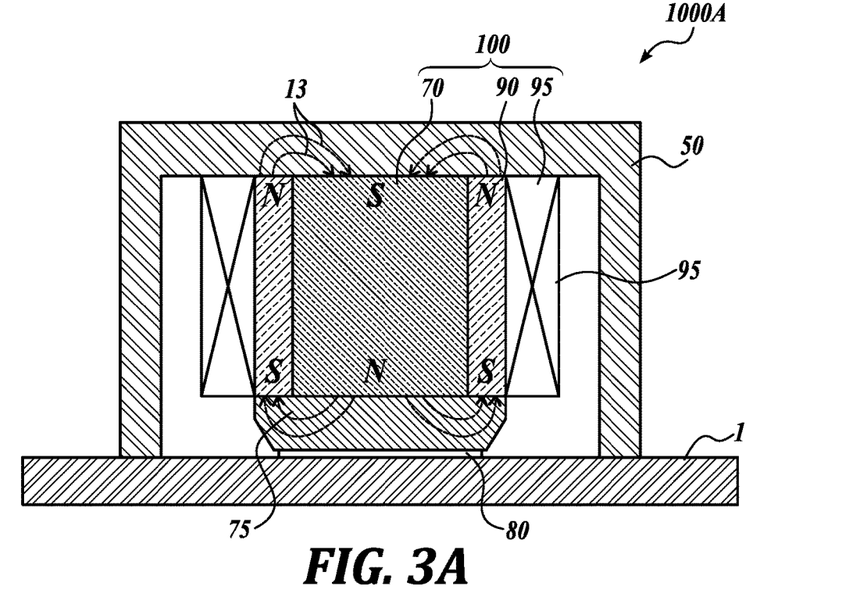
FIGS. 3A and 3B are schematic views of an EMAT in the transportation and operational configurations, respectively, in accordance with embodiments of the presently disclosed technology.
Figure 3B:
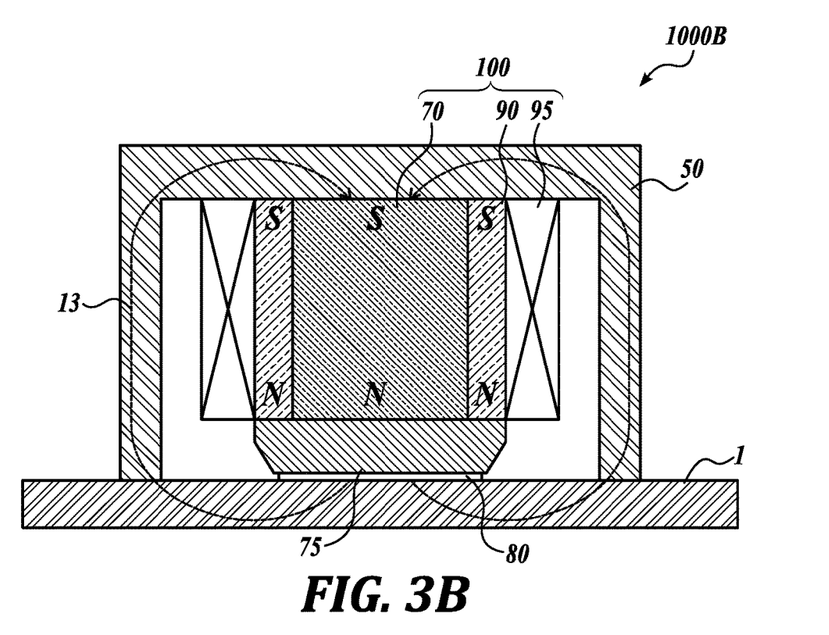

FIGS. 3A and 3B are schematic views of an EMAT in the transportation and operational configurations, respectively, in accordance with embodiments of the presently disclosed technology. The illustrated EMAT 1000A/1000B includes a concentric arrangement of a hard magnet (also referred to as a "permanent magnet") 70 and a soft magnet 90 (which can be switchably polarized by a pulse of electrical current). Winding a magnetic coil 95 around both the hard magnet 70 and the soft magnet 90 provides a more compact assembly. Collectively, the hard magnet 70, the soft magnet 90, and the magnetic coil 95 are referred to as electro-permanent magnet (EPM) 100. The magnets 70/90 having circular cross-section, elliptical cross-section, rectangular cross-section, or other cross-section shapes may be arranged in a concentric or a co-axial arrangement, or their axes may be parallel (e.g., bi-axial arrangement). In some embodiments, the hard magnet 70 may be made of Neodymium and the soft magnet may be made of softer material such as Alnico, but other materials are also possible. In the illustrated embodiment, the hard magnet 70 is surrounded by the soft magnet 90, but the embodiments having the hard magnet 70 surrounding the soft magnet 90 are also possible. Furthermore, the illustrated hard magnet 70 and/or the soft magnet 90 are continuous, but modular hard magnets and/or soft magnets (e.g., including several parts) are also possible.

FIG. 3A illustrates the EMAT 1000A with the soft magnet 90 that is magnetized (polarized) in the opposite direction than that of the hard magnet 70. In some embodiments, a pulse of electrical current or constant electrical current is injected into a magnetic coil 95 to change polarization (to polarize) of the soft magnet 90. In some embodiments, a current pulse of about 10 ms suffices to polarize the soft magnet 90. In at least some embodiments, the magnetic flux 13 is "shorted" through a yoke 50 and a shoe 75, while eliminating or at least reducing the magnetic flux 13 through the steel substrate (specimen) 1. In this polarity, the EMAT 1000A may be suitable for shipping because of the reduced electromagnetic flux 13 outside of the EMAT 1000A.

FIG. 3B illustrates the EMAT 1000B with the soft magnet 90 that is magnetized (polarized) in the direction of the hard magnet 70 (e.g., using a pulse of electrical current opposite from the one used for the EMAT 1000A arrangement). In some embodiments, the magnetic flux 13 propagates through a shoe 75 and a sensor coil 80. The interaction of the magnetic flux 13 with the AC current in the sensor coil 80 leads to Lorenz forces in the pipe 1, in turn causing the acoustic waves in the pipe 1 that may reflect from the flaws in the pipe. The reflected acoustic waves (if any) cause the opposite sequence of acoustic/electric/magnetic reactions, which ultimately indicates presence, type and/or size of the flaw. In at least some embodiments, the coaxial arrangement of the magnets of the EPM 100 decreases the size of the EMAT 1000, while increasing density of the magnetic flux 13. The shoe 75 and the yoke 50 may be made of suitable ferromagnetic materials, for example of ferromagnetic steels.

Figure 4:
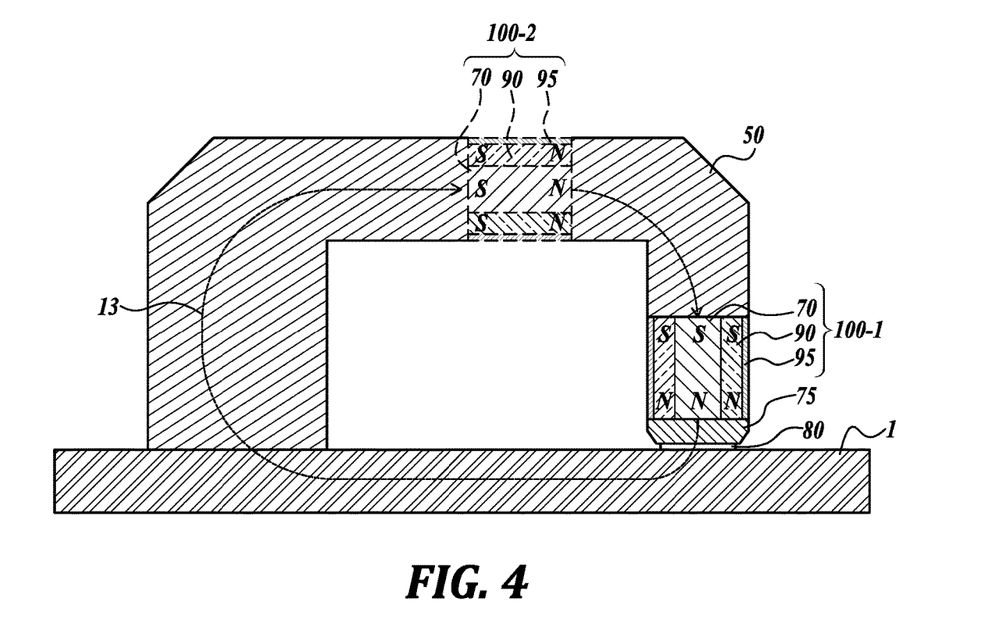
FIG. 4 is a schematic view of alternative locations of the magnets of an EMAT in accordance with embodiments of the presently disclosed technology.

FIG. 4 is a schematic view of alternative locations of the EPMs of an EMAT in accordance with embodiments of the presently disclosed technology. Since the magnetic flux 13 propagates through the yoke 50, in at least some embodiments, the EPM 100 may reside in different locations without significantly affecting the performance of the EMAT. For example, the EMAT that uses EPM 100-2 may have similar performance as the EMAT that uses EPM 100-1. In some embodiments, both EPMs 100-1 and 100-2 may be used in operation. In some embodiments, more than two EPMs may be used in operation.

Figure 5A:
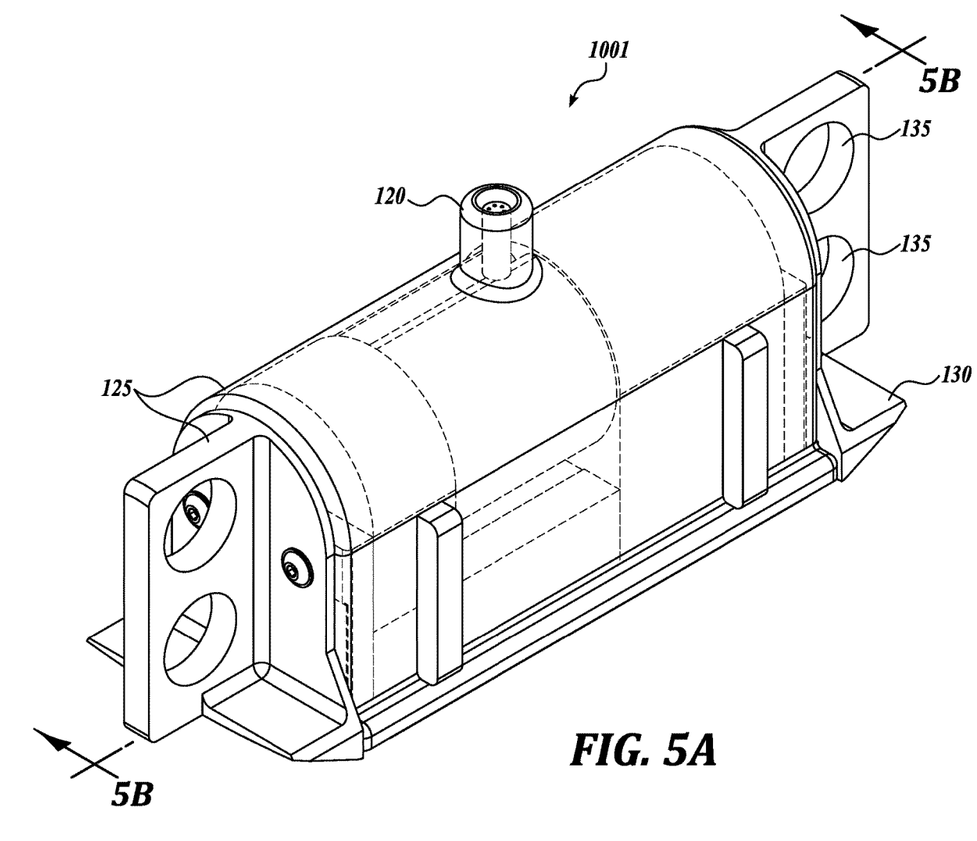
FIG. 5A is an isometric view of an EMAT in accordance with embodiments of the presently disclosed technology.

FIG. 5A is an isometric view of an EMAT 1001 in accordance with embodiments of the presently disclosed technology. The illustrated EMAT 1001 includes a chassis 125 for housing the internal components. The chassis 125 may include guides 135 for driving the EMAT through the pipe under inspection (or over other specimen under inspection) and wear pads 130 for sliding the EMAT 1001 in the pipe. The chassis 125 may also include a connector 120 for providing power/signal paths into/out-of the EMAT 1001. The interior of the EMAT 1001 is described below with reference to FIG. 5B.

Figure 5B:
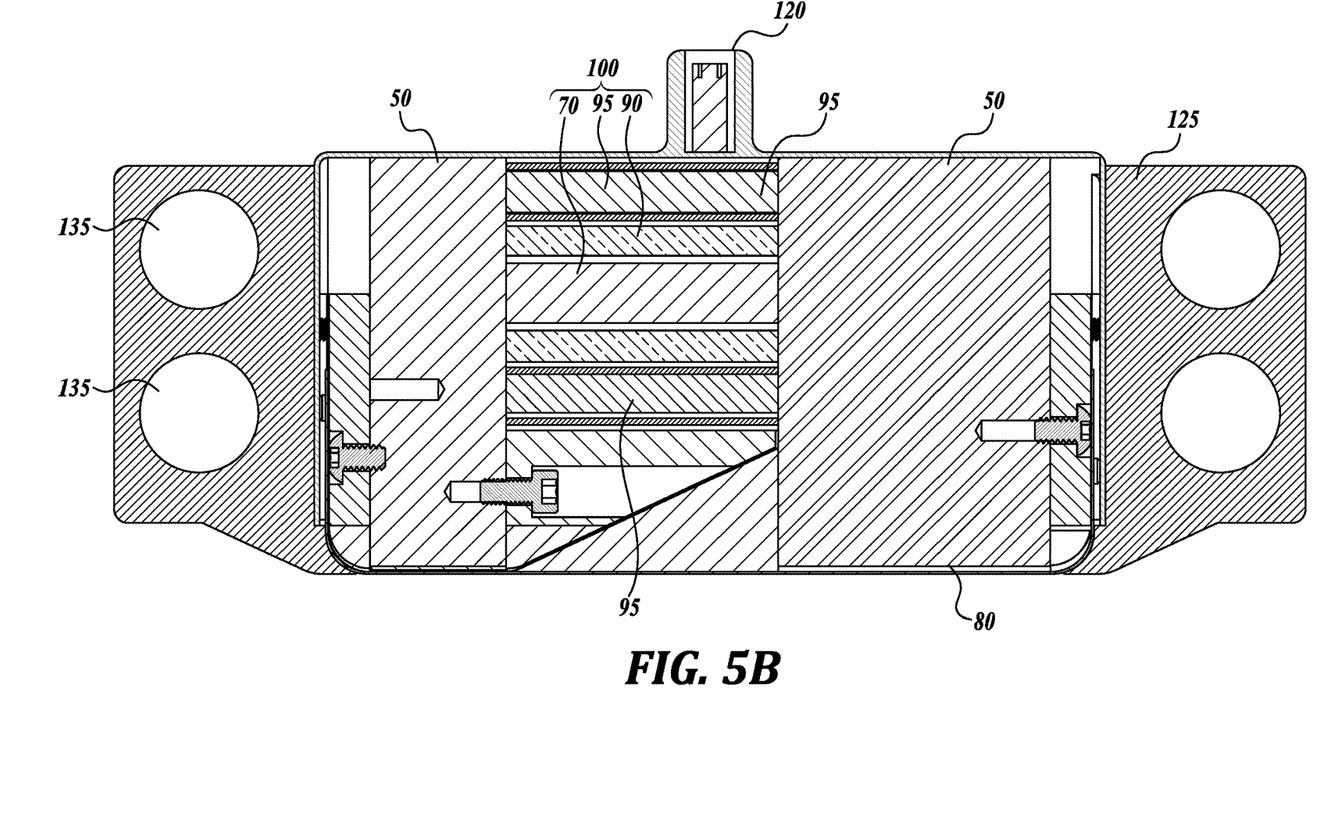
FIG. 5B is a cross-sectional view of the EMAT illustrated in FIG. 5A.

FIG. 5B is a cross-sectional view of the EMAT illustrated in FIG. 5A. The EPM 100 includes the hard magnet 70, the soft magnet 90, and the magnetic coil 95. The polarity of the soft magnet 90 can be changed by a pulse of current or constant current through the magnet coil 95. For example, the polarity of the soft magnet 90 and the hard magnet 70 may be the same when making the measurements, while their polarity may be the opposite for the shipping/storage of the EMAT. In some embodiments, the yoke 50 is modular, i.e., the yoke may include several ferromagnetic parts that conduct magnetic flux toward the sensor coil 80 and further into the specimen under test.

Figure 6A:
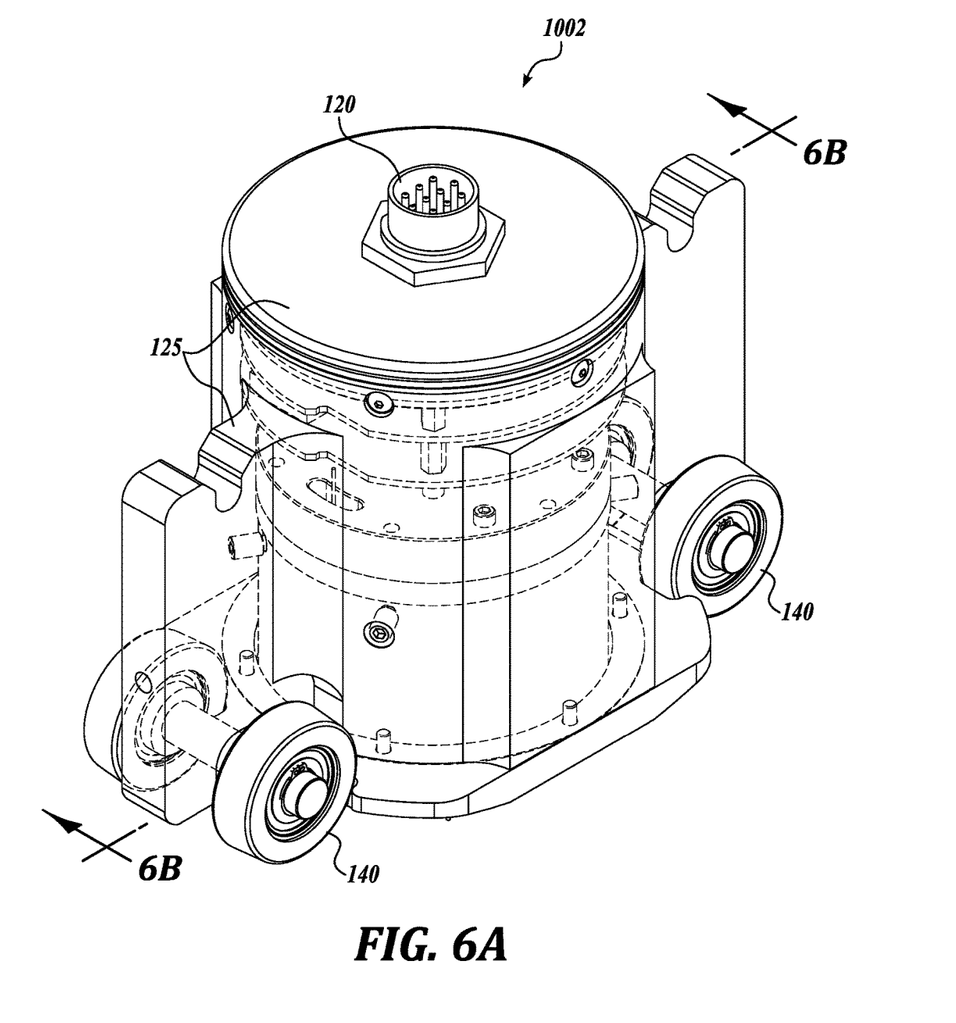
FIG. 6A is an isometric view of an EMAT in accordance with embodiments of the presently disclosed technology.

FIG. 6A is an isometric view of an EMAT 1002 in accordance with embodiments of the presently disclosed technology. The EMAT 1002 includes the chassis 125 having wheels 140 for, for example, moving the EMAT 1002 inside the pipe under inspection. The connector 120 can provide power/signal paths for the EMAT 1002. The interior of the EMAT 1002 is described below with reference to FIG. 6B.

Figure 6B:
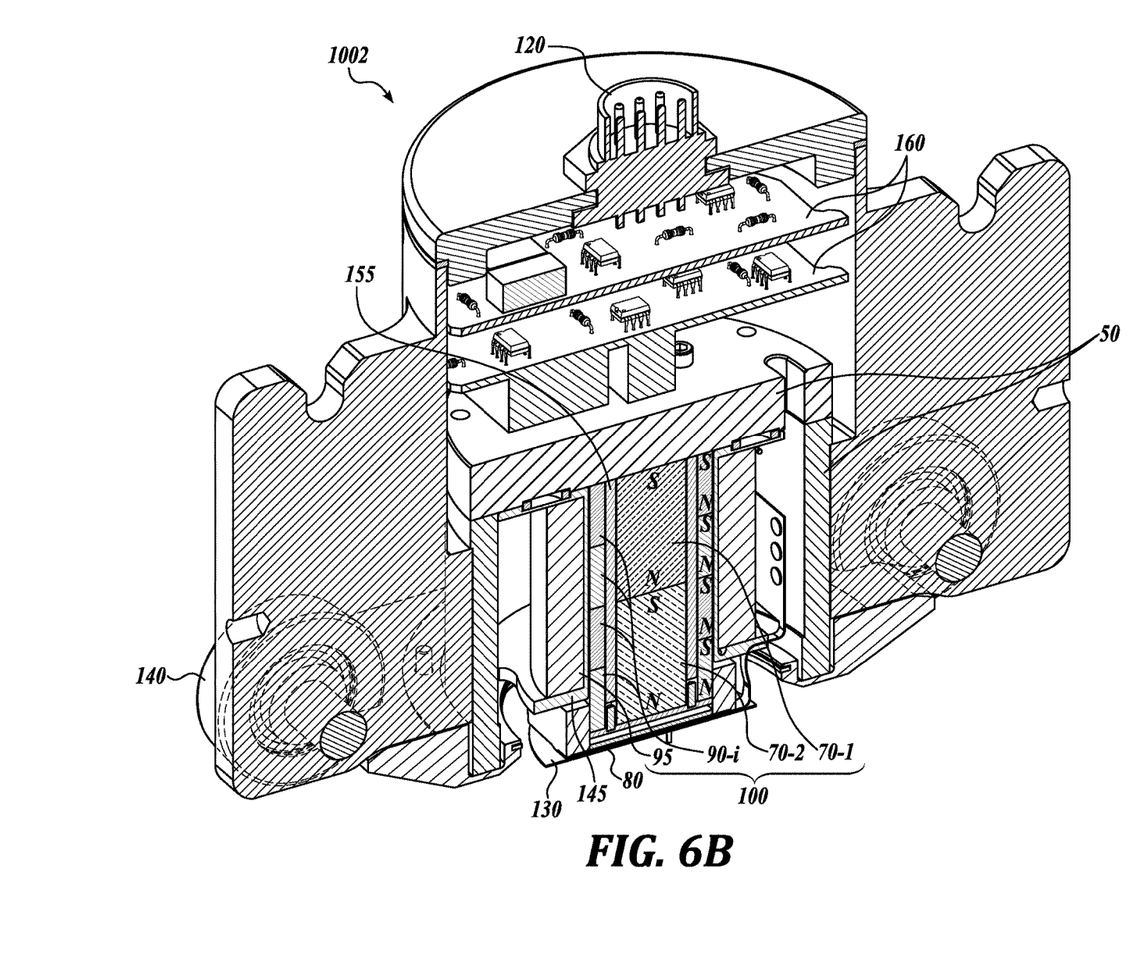
FIG. 6B is a cross-sectional view of the EMAT illustrated in FIG. 6A.

FIG. 6B is a cross-sectional view of the EMAT illustrated in FIG. 6A. In some embodiments, the EPM 100 includes the magnetic coil 95, several hard magnets **70-*i* and/or several soft magnets 90-*i*** in a stacked arrangement. Such modular design may lower the cost of the magnets or may facilitate easier assembly.

The soft magnets **90-*i* are at least partially surrounded by the magnet coil 95 that can set the polarity of the soft magnets 90-*i*. For example, with the polarity of the hard magnets 70-*i* and the soft magnets 90-*i* as illustrated in FIG. 6B, the magnetic flux density through the sensor coil 80 is increased, resulting in stronger signal in the specimen (e.g., pipe). To prepare the EMAT 1002 for transportation or for repositioning in the pipe, the polarity of soft magnets 70-*i* can be reversed by sending a current pulse through the magnet coil 95. In some embodiments, the EMAT 1002 includes a spool 145 for housing the magnet coil 95**.

The EMAT 1002 may include electronics 160 for controlling the operation, data acquisition, data processing, and/or other purposes. In some embodiments, the sensor coil 80 is protected by a wear pad 130 between the specimen and the sensor coil 80.

Figure 7A:
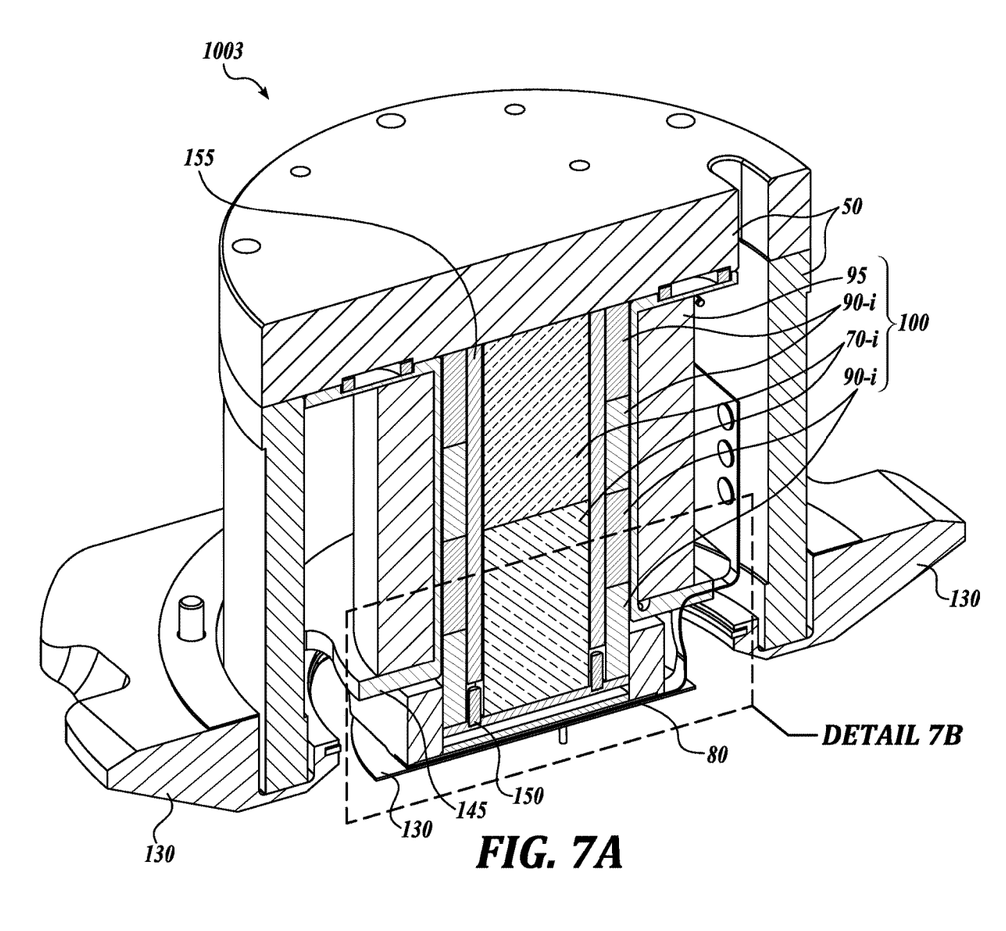
FIG. 7A is an isometric cross-sectional view of an EMAT in accordance with embodiments of the presently disclosed technology.

FIG. 7A is an isometric cross-sectional view of an EMAT 1003 in accordance with embodiments of the presently disclosed technology. In the illustrated embodiment, the yoke 50 also serves, at least partially, as the chassis of the EMAT 1003. The power/signal to the EMAT 1003 may be routed through a connector (not shown) on the side surface of the yoke 50. In some embodiments, the EMAT 1003 may have about 3" diameter, and about 2.5" height. In some embodiments, the diameters of the hard magnet 70 and the soft magnet 90 may be about 0.6" and 1", respectively.

Figure 7B:
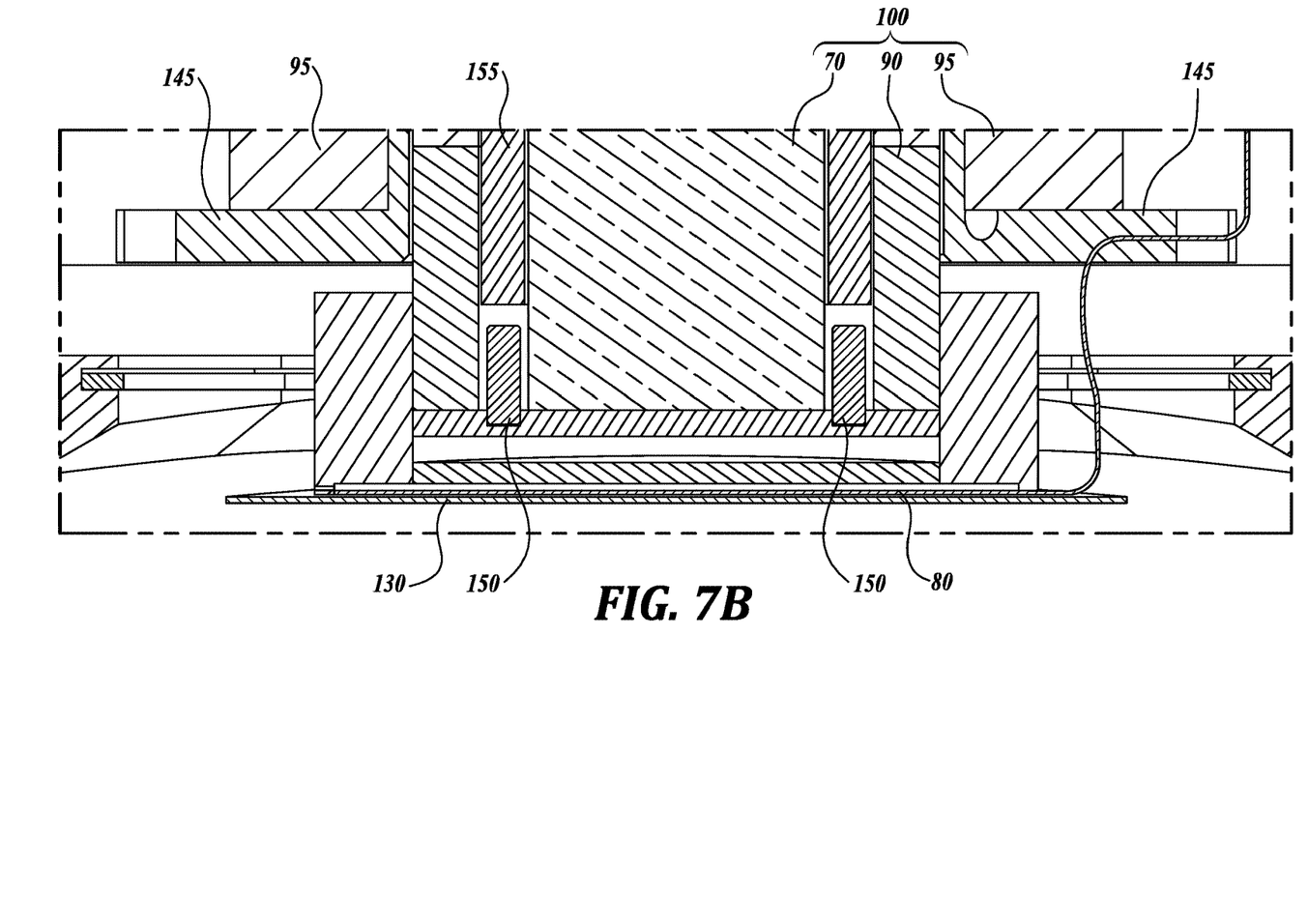
FIG. 7B is a detail view of the EMAT illustrated in FIG. 7A.

FIG. 7B is a detail view of the EMAT illustrated in FIG. 7A. In some embodiments, the hard magnets 70-*i* are separated from the soft magnets 90 with a spacer 155. The hard magnet 70 and the soft magnet 90 may be secured inside the EMAT by one or more pins 150.

Figure 8:
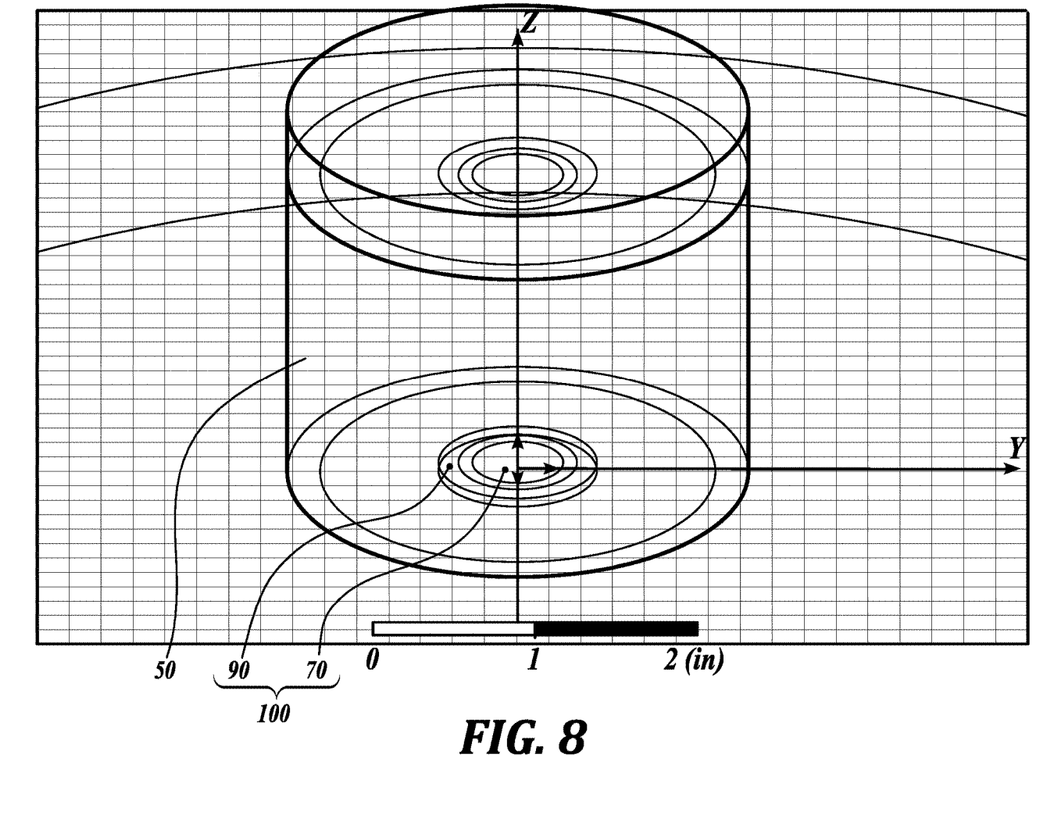
FIG. 8 is a geometrical model used in electromagnetic simulation of an EMAT in accordance with embodiments of the presently disclosed technology.

FIG. 8 is a geometrical models used in electromagnetic simulation of an EMAT in accordance with embodiments of the presently disclosed technology. In the illustrated model, the hard magnet 70 is represented as a solid cylinder having a vertical axis in a Z direction, and a base in the XY plane. The soft magnet 90 is represented as a circular shell that surrounds the hard magnet 70. The yoke 50 surrounds both magnets 70 and 90.

Figure 9A:
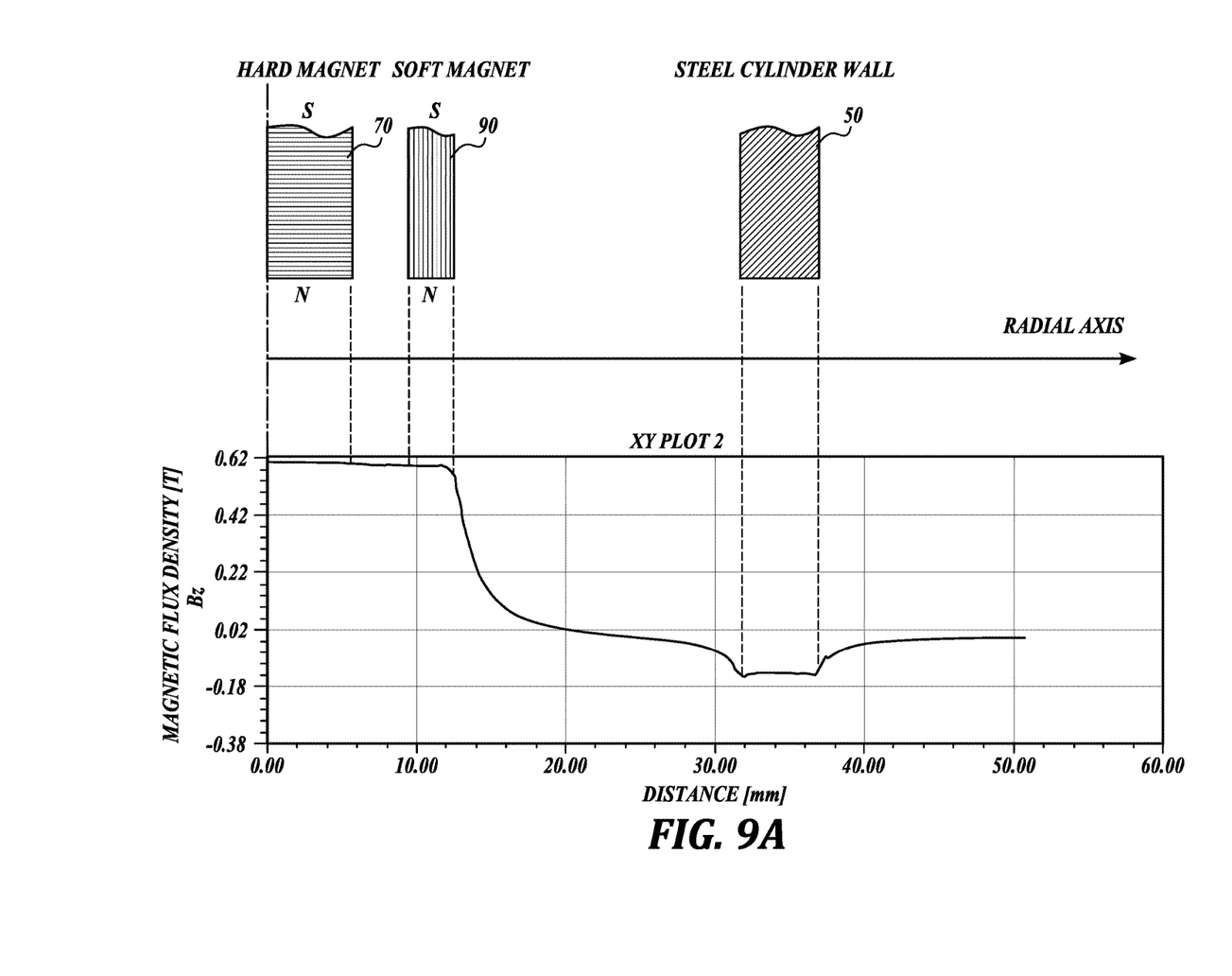
FIGS. 9A and 9B are graphs of simulation results of magnetic fields of an EMAT in accordance with the embodiments of the presently disclosed technology.
Figure 9B:
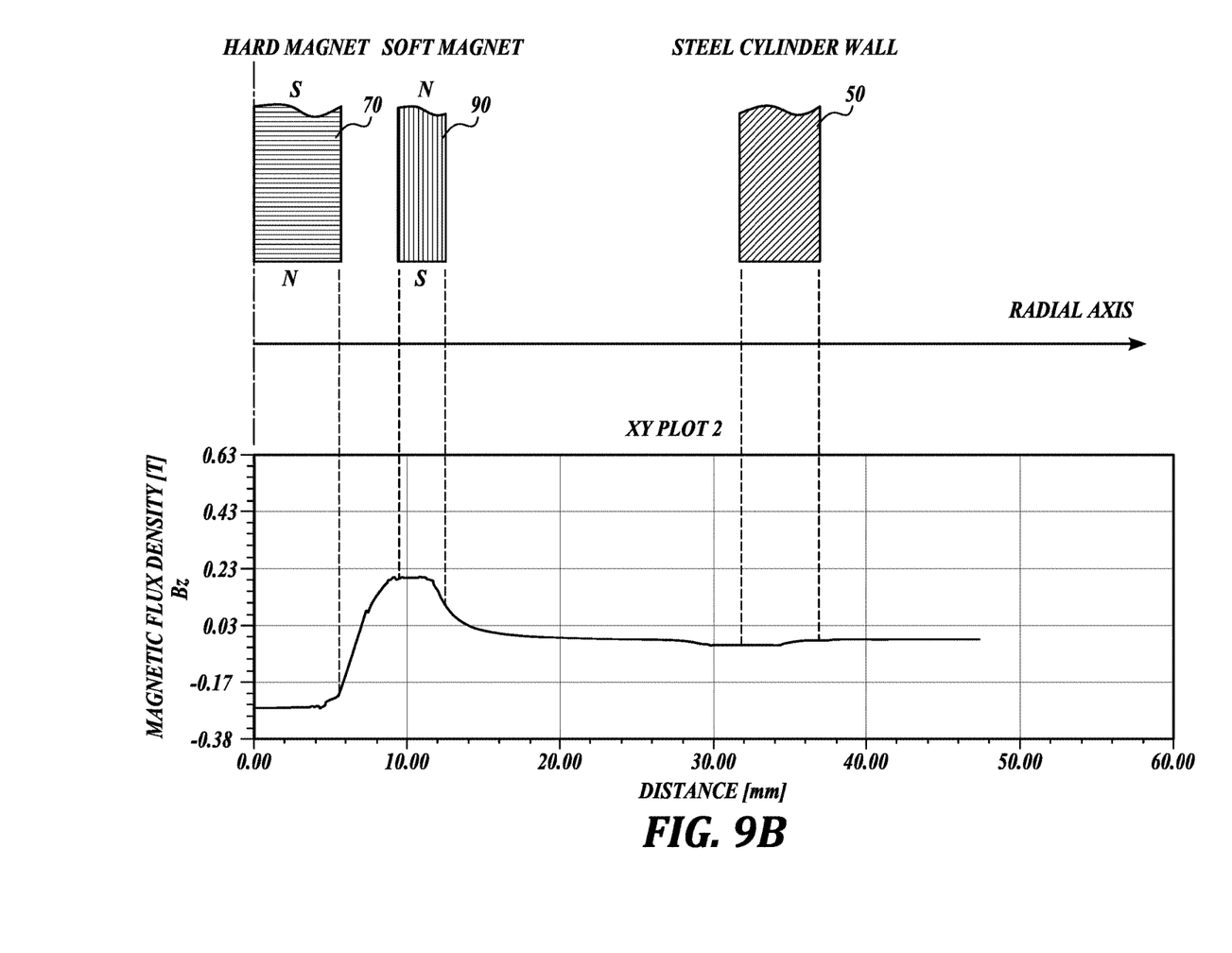

FIGS. 9A and 9B are graphs of simulation results of magnetic fields of an EMAT in accordance with the embodiments of the presently disclosed technology. In both figures, the horizontal axis represents the axial distance in mm from the centerline of the hard magnet. The vertical axis represents the magnetic flux density in T at a horizontal plane at the top of the pipe (specimen). The hatched shapes above the graph indicate the locations of the hard magnet 70, the soft magnet 90, and the yoke 50.

In the graph of FIG. 9A, the N-S polarization of the hard magnet 70 and the soft magnet 90 are the same. As a result, the magnetic flux density at the hard magnet 70 and the soft magnet 90 is relatively high—about 0.6 T. Therefore, the magnetic flux density at the sensor coil 80 (not shown) is also very high, which is suitable for making the measurements. Further away from the magnets, at the location of the yoke 50, the magnetic flux density is relatively small, e.g., close to zero.

In the graph of FIG. 9B, the N-S polarization of the hard magnet 70 and the soft magnet 90 are opposite. As a result, the magnetic flux density below the hard magnet 70 and the soft magnet 90 is relatively low—about −0.22 T for the hard magnet 70, and about +0.22 for the soft magnet 90. The average of the magnetic flux density under the magnets 70/90 is close to zero indicating that the magnetic flux propagates from, for example, N pole of the hard magnet 70 to the S pole of the soft magnet 90, thus minimizing or at least reducing magnetic interactions with the objects in the vicinity of the EMAT. Furthermore, the magnetic flux density at the sensor coil 80 is also relatively small on average. Therefore, the illustrated pair of the hard magnet 70 and soft magnet 90 may be suitable for transportation and/or repositioning the EMAT.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

We claim:

1. An electromagnetic acoustic transducer (EMAT), comprising:
    an electro-permanent magnet (EPM) configured to controllably apply a biasing magnetic flux to a target location, comprising:
        a hard magnet,
        a soft magnet at least partially enclosing the hard magnet, and
        a magnetizing coil having a plurality of turns at least partially encircling the soft magnet and the hard magnet, wherein the magnetizing coil is configured to controllably magnetically bias the soft magnet when a current is applied to the magnetizing coil; and
    a sensor coil configured to provide an alternating magnetic field to the target location,
    wherein the EMAT is configured to controllably coordinate the EPM and the sensor coil to perform non-destructive testing of the target location.

2. The EMAT of claim 1, wherein the hard magnet, the soft magnet, and the magnetizing coil are coaxially aligned perpendicular to the target location.

3. The EMAT of claim 1, wherein the hard magnet, the soft magnet, and the magnetizing coil are coaxially aligned parallel to the target location.

4. The EMAT of claim 1, further comprising a yoke providing magnetic communication between a first end and a second end of the EPM.

5. The EMAT of claim 1, wherein the yoke is made of a ferromagnetic material.

6. The EMAT of claim 5, wherein the ferromagnetic material comprises steel.

7. The EMAT of claim 4, wherein the yoke partially encloses the EPM.

8. The EMAT of claim 1, further comprising a chassis configured to at least partially house the EPM.

9. The EMAT of claim 8, wherein the chassis comprises wheels configured to move the EMAT along the target surface.

10. The EMAT of claim 8, wherein the chassis comprises skid pads configured to move the EMAT along the target surface.

11. The EMAT of claim 1, further comprising control electronics configured to control the EPM and the sensor coil in order to perform ultrasonic non-destructive testing at the target location.

12. The EMAT of claim 1, further comprising an electrical connector configured to provide electrical connection between the EMAT and a power source and/or controller housed separately from the EMAT.

13. A method of operating an electromagnetic acoustic transducer (EMAT), comprising:
  passing a first pulse of electrical current through a magnetizing coil adjacent to a soft magnet of an electro-permanent magnet (EPM);
  in response to passing the first pulse of electrical current, polarizing the soft magnet to a first polarization, wherein the soft magnet at least partially encloses a hard magnet of the EPM, and wherein the hard magnet is in the first polarization;
  passing a second pulse of electrical current through the magnetizing coil adjacent to the soft magnet;
  in response to passing the second pulse of electrical current, polarizing the soft magnet to a second polarization, wherein the second polarization is opposite from the first polarization.

14. The method of claim 13, further comprising directing a magnetic flux to a sensor coil of the EMAT.

15. The method of claim 14, further comprising generating acoustic waves to perform a non-destructive testing of a specimen at a target location.

16. The method of claim 15, further comprising detecting a flaw in the specimen based on reflected acoustic waves.

17. The method of claim 15, wherein passing the first pulse of electrical current is done in preparation for the non-destructive testing of the specimen.

18. The method of claim 13, wherein passing the second pulse of electrical current is done in preparation for repositioning or shipping of the EMAT.

19. The method of claim 13, further driving an alternating current through a sensor coil of the EMAT to provide an alternating magnetic field at a target location.

20. The method of claim 13, wherein the magnetizing coil at least partially encircles the soft magnet.

21. The method of claim 13, wherein the hard magnet and the soft magnet are co-axial.

22. The method of claim 13, wherein the hard magnet and the soft magnet are concentric.

23. The method of claim 13, wherein the hard magnet and the soft magnet are bi-axial.

24. The method of claim 13, wherein the hard magnet and the soft magnet are cylindrical.

* * * * *